United States Patent [19]
Fetheroff

[11] 4,150,577
[45] Apr. 24, 1979

[54] COMPUTER CONTROLLED ULTRASONIC DEFECT GATE

[75] Inventor: Charles W. Fetheroff, Willowick, Ohio

[73] Assignee: TRW Inc., Cleveland, Ohio

[21] Appl. No.: 869,958

[22] Filed: Jan. 16, 1978

[51] Int. Cl.² .............................................. G01N 29/04
[52] U.S. Cl. .......................................... 73/611; 73/612
[58] Field of Search ................ 73/609, 610, 611, 612, 73/613

[56] References Cited
U.S. PATENT DOCUMENTS

| | | | |
|---|---|---|---|
| 3,791,199 | 2/1974 | Toth et al. | 73/609 |
| 3,986,389 | 10/1976 | Mesina et al. | 73/611 |
| 4,054,053 | 10/1977 | Yamamoto et al. | 73/610 X |
| 4,058,001 | 11/1977 | Waxman | 73/620 |

*Primary Examiner*—James J. Gill

[57] ABSTRACT

An ultrasonic inspection system including a defect gate which can be interfaced with a digital computer. A high frequency precision oscillator and two preset counters define the start and duration of a gate period or window corresponding to an inspection depth range within the test specimen. The magnitudes and locations of the two or more largest defect indications within a gate window are determined and made available to the computer for analysis and diagnosis. A rear interface gate window is provided and a determination is made as to the presence or absence within the rear interface gate window of a signal representing the rear interface of the specimen. The distance between the interrogating transducer and the test specimen front interface is also determined at each point. Means are provided for real time control of the inspection system parameters by the computer to allow adaptive control of the inspection process based on real time diagnosis of the test data.

14 Claims, 6 Drawing Figures

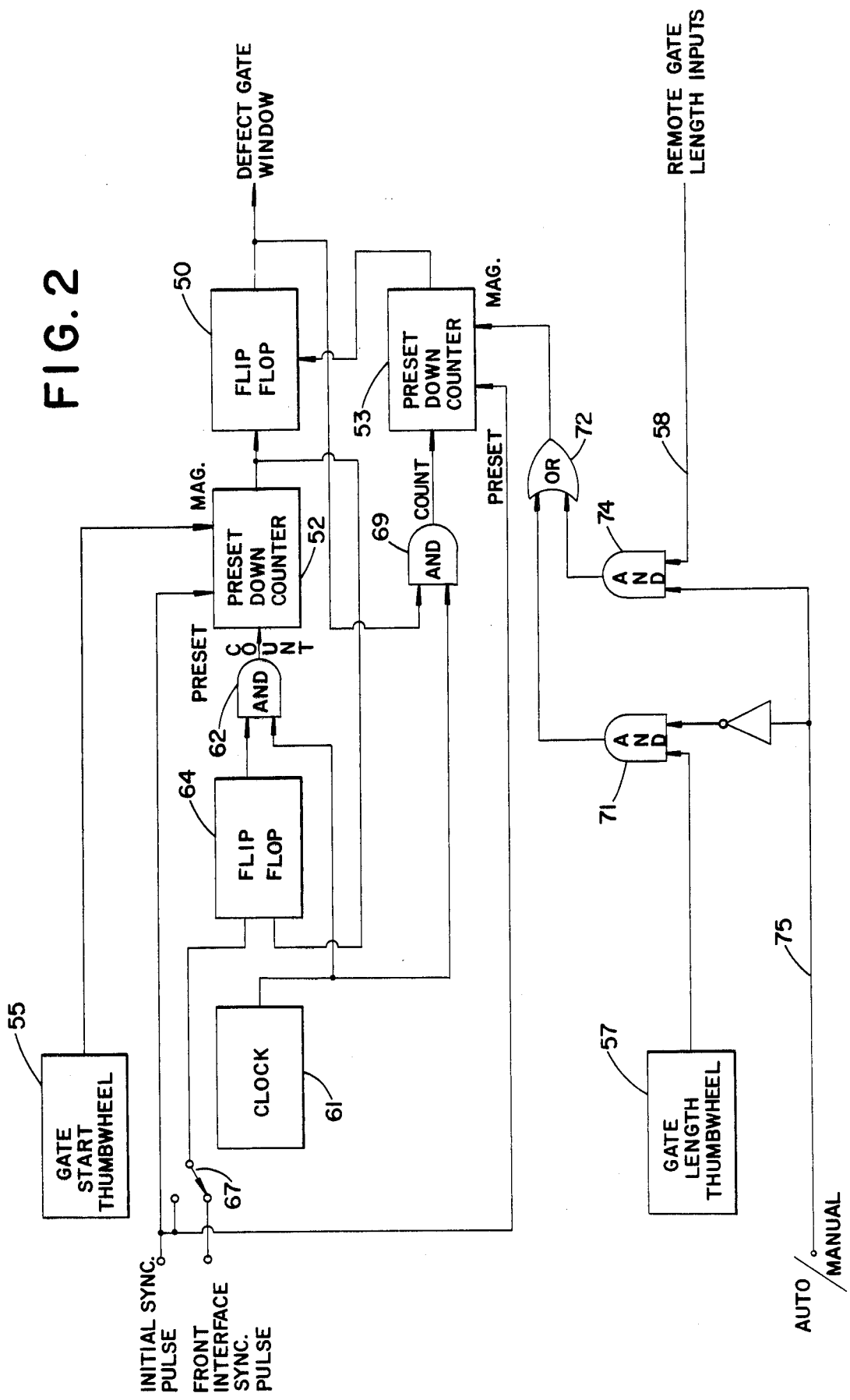

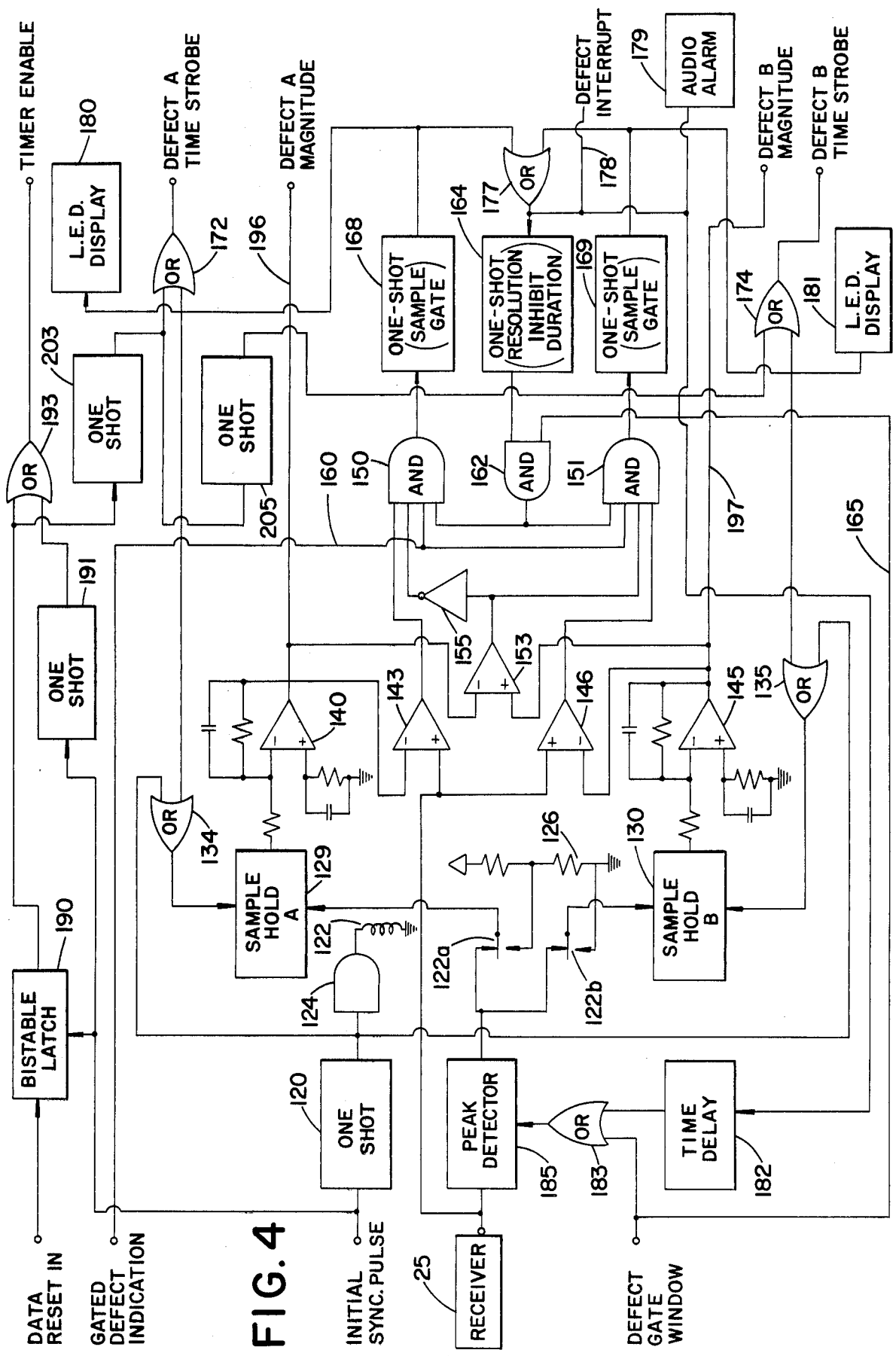

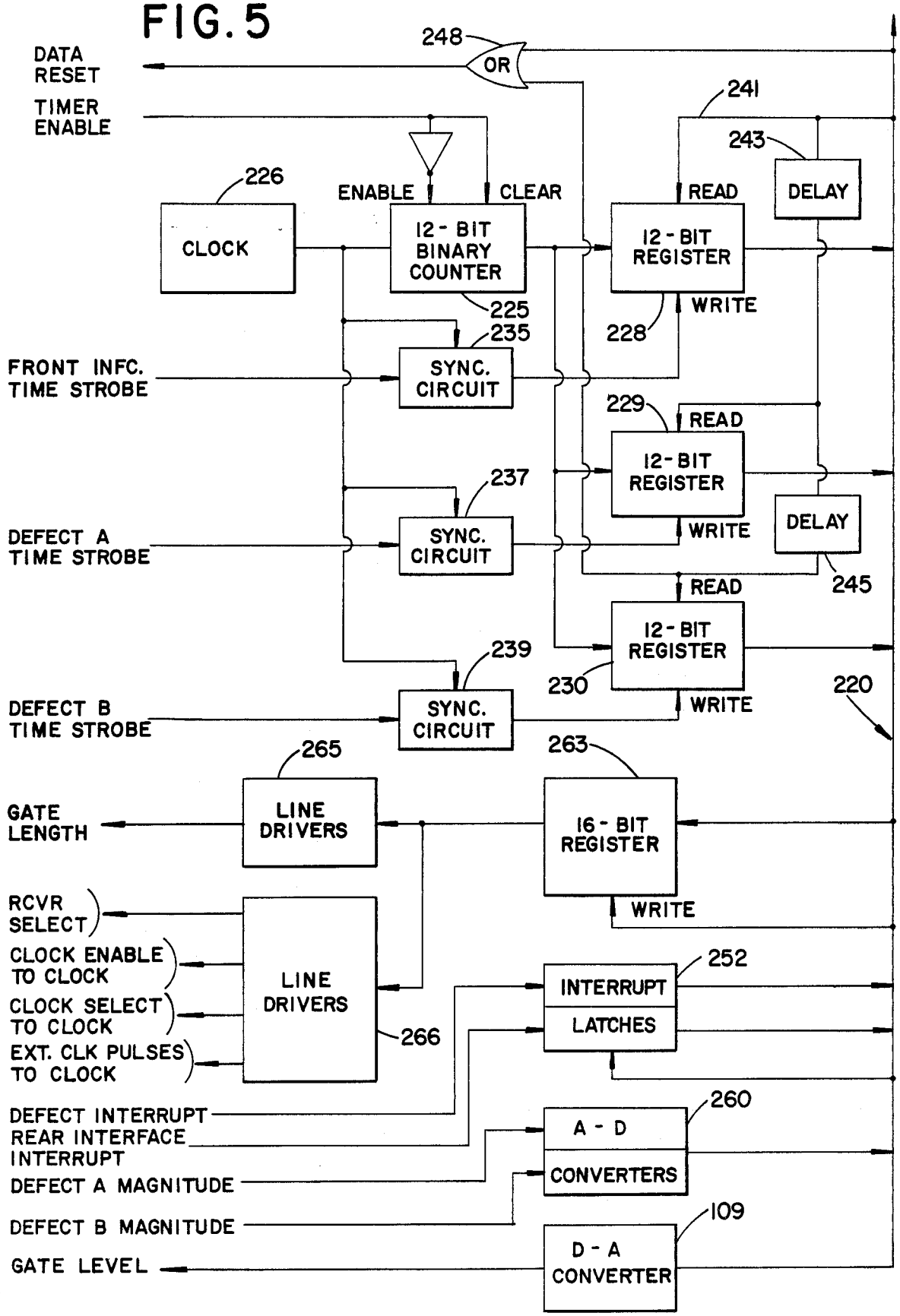

COMPUTER CONTROLLED ULTRASONIC DEFECT GATE

GOVERNMENT CONTRACT

The invention herein described was made in the course of or under a contract or subcontract thereunder with the U.S. Air Force.

BACKGROUND OF THE INVENTION

This invention relates to ultrasonic nondesctructive testing. More particularly, the invention concerns a defect gate which obtains data regarding defects in a test specimen and which can be interfaced with a computer for control of the inspection parameters and for analysis and diagnosis of the data.

Ultrasonic nondestructive evaluation techniques are based on transmission and reflection of acoustic energy in a material under test. Interrogating signals are transmitted to a material specimen and reflected from discontinuities therein, which may be indicative of defects in the specimens. In conventional ultrasonic inspection of materials, an operator manually adjusts the instrumentation parameters while observing a display of the transmitted and/or reflected signal characteristics. To distinguish those signal characteristics indicative of specimen defects the operator synchronizes a defect gate "window" with a signal to detect only indications from the region of interest in the specimen being inspected. The gate window corresponds to a depth range in the test specimen. Precise adjustment is often required, as when defects may occur very near the front and rear specimen surfaces and/or where the geometry of the specimen under test is such that reflection from "valid" discontinuities within the specimen may be expected. The operator also manually adjusts the defect gate "level" above which a defect indication is regarded as significant.

During the ultrasonic inspection process the operator must continually monitor the indications obtained and readjust various settings. This obviously results in a slow and expensive procedure subject to human errors, lack of repeatability and limited data analysis and diagnostics.

To some extent the human operator has been supplemented by automatic data gathering and control procedures which may involve the use of a computer. Typically, data as to a defect detected within a gate window is converted to digital form and made available to a computer. Again, however, where complex specimen geometries are involved and defects may occur close to valid discontinuities, the problem of distinguishing a defect from such a valid discontinuity remains. The data captured may prove, upon analysis, to be from a valid discontinuity. Further, in case of multiple defects which are relatively closely spaced and within the same gate window, only one such defect will be captured.

SUMMARY OF THE INVENTION

According to the present invention, there is provided an ultrasonic defect gate which can be interfaced directly with a computer and which detects the two or more largest defect indications appearing within a defect gate window. Both the magnitudes and locations of these two or more largest defects are made available to a computer for analysis and diagnosis. Thus, a defect will not go undetected if it occurs near a "valid" discontinuity in the specimen and a plurality of relatively closely spaced defects will be detected.

Provision is made for inhibiting the detection of a defect within a predetermined time following the detection of a previous defect within the same gate window. This prevents indication of two defects which are so closely spaced that it is advantageous to consider them as a single defect.

Provision is also made for determining the distance between the interrogating transducer and the specimen front interface.

A defect gate embodying the present invention also provides very precise synchronization of a defect gate window within the test specimen. Pulses from a stable high frequency crystal controlled clock are fed to a pair of preset down counters to define the start point and duration of the gate window. The counters are presettable manually or under computer control.

This invention also provides an additional gate window following the defect gate window and where a signal reflection from the rear interface of the specimen may be expected. The presence or absence of a rear interface indication within the rear interface gate window is monitored and such data is made available to the computer. The information aids the computer in analyzing the data obtained within the defect gate window.

A computer interface provides for real time control of the inspection parameters by the computer. This allows adaptive control of the inspection process based on real time computer diagnosis of the test data.

BRIEF DESCRIPTION OF THE DRAWINGS

FIG. 2 is a block diagram of a circuit for defining the defect gate window;

FIG. 4 is a block diagram of the circuit portions of the defect gate for detecting and storing the magnitudes of the two largest defect indications within a gate window;

FIG. 5 is a block diagram of the circuit portions of the defect gate which interface with a digital computer.

DESCRIPTION OF A PREFERRED EMBODIMENT

Figure 1:
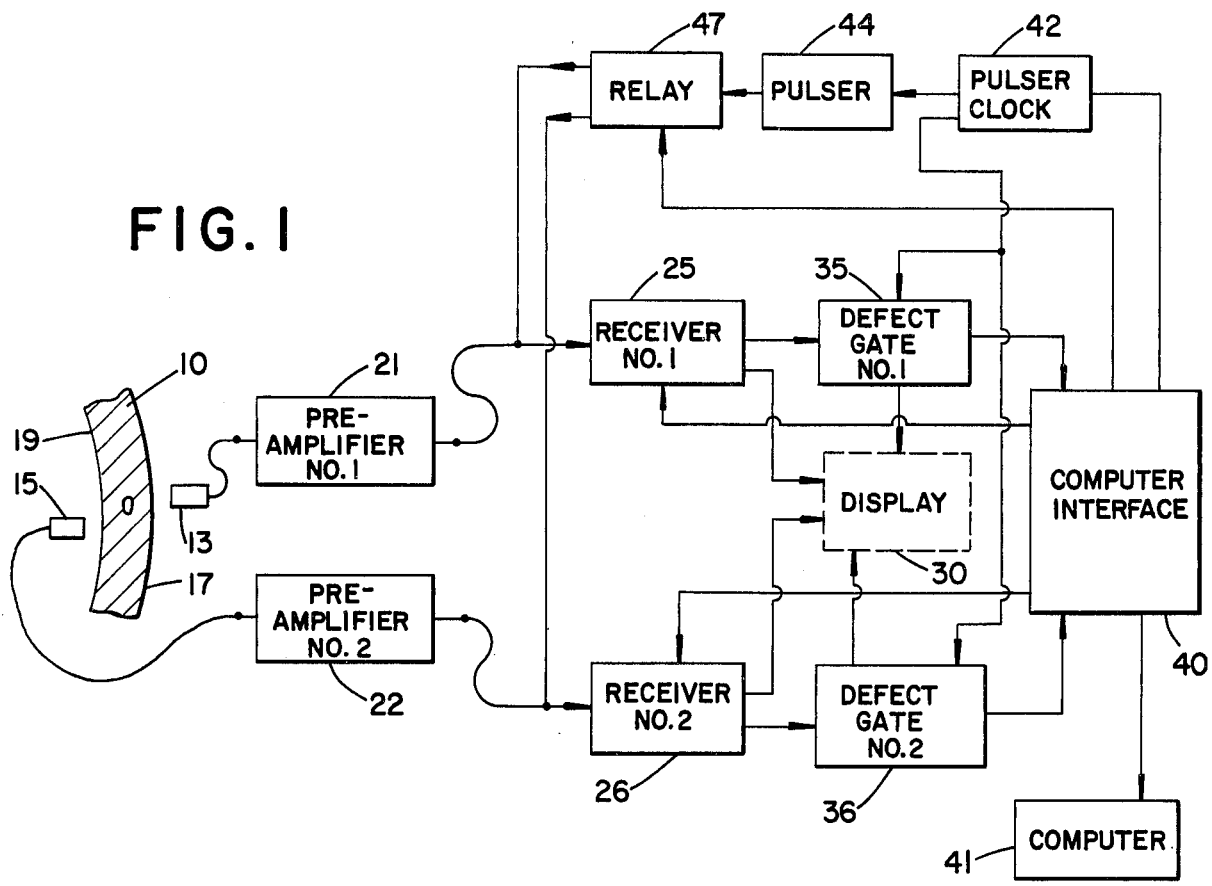
FIG. 1 is a block diagram of an ultrasonic inspection system embodying the present invention.

There is shown in FIG. 1 an ultrasonic inspection system for inspecting a specimen 10 which may be, for example, a turbine disk. An ultrasonic interrogating pulse is applied periodically to the specimen 10 through one or the other of two electromechanical transducers 13 and 15. The pulse passes through specimen 10 from the front interface 17 to the rear interface 19 and is reflected from any discontinuities therein. The reflections may represent defects in the specimen or may represent "valid" discontinuities such as the interfaces 17 and 19. The front interface 17 and rear interface 19 have been identified with respect to transducer 13. It will be appreciated that the two interfaces would be interchanged from the point of view of transducer 15 in FIG. 1. Both transducers may, of course, be on the same side of the specimen or only one transducer may be employed when circumstances dictate.

Each reflected pulse passes through either transducer 13 or 15 and associated preamplifier 21 or 22 to receiver 25 or 26. Each receiver applies its output to a display unit 30 and also to a defect gate 35 or 36. Each defect gate 35, 36 operates to detect potential specimen defect indications in its receiver output signal within predetermined depth boundaries in the specimen. Each gate acquires the amplitude and location data for the two largest defects within the gate bounds and makes such information available through a computer interface 40 to a computer 41 for processing.

Electrical exciting pulses are supplied to transducers 13 and 15 at intervals determined by a pulser clock 42. At selected intervals the pulser clock supplies a triggering pulse to a pulser 44 which develops an exciting pulse of the proper characteristics for transducers 13 and 15. Each exciting pulse is directed through relay 47 to one or the other of transducers 13 and 15. The desired transducer and the rate at which triggering pulses are supplied from pulser clock 42 may be selected manually or under control of the computer through computer interface 40.

FIGS. 2–5 illustrate the circuits employed for one of the defect gates 35, 36. These circuit will be described in terms of defect gate 35 but it will be understood that defect gate 36 is substantially the same in all respects.

The circuit of FIG. 2 defines a gate time "window" which corresponds to a depth range in the test specimen. The specimen is examined for defects within the range. The circuit includes a flip-flop 50 and a pair of preset down counters 52 and 53. A count corresponding to the desired starting point of a gate window is provided to counter 52 from a gate start thumbwheel 55. A count corresponding to the desired duration of the gate window is provided to counter 53 through either a gate length thumbwheel 57 or from the computer through line 58. Each counter 52, 53 is preset upon receipt of an initial sync pulse which is essentially a pulse from pulser clock 42 (FIG. 1). Pulses are provided to counter 52 from a high frequency clock pulse generator 61 through a gate 62 when the gate is enabled by a flip-flop 64. Flip-flop 64 is set according to the position of manual switch 67 either by the initial sync pulse or by a front interface sync pulse. The latter pulse is generated when the ultrasonic interrogating pulse is reflected from the front interface of the specimen. When flip-flop 64 is set clock pulses from generator 61 pass through AND gate 62 and decrement counter 52. When counter 52 reaches zero it provides an output which sets flip-flop 50 and resets flip-flop 64. The set condition of flip-flop 50 defines the gate window. Flip-flop 50, when set, enables AND gate 69 to pass pulses from clock generator 61 to counter 53. When counter 53 reaches zero flip-flop 50 is reset and the gate window is terminated.

The frequency of pulses from clock pulse generator 61 preferably is selected so that one clock period corresponds to the time required for 10 mils of ultrasonic wave propagation within the test specimen. The gate starting point and duration may, therefore, be set in counters 52 and 53 in terms of mils or inches below the part surface when flip-flop 64 is set by a front interface sync pulse. The starting point may be defined by a two digit BCD number and the duration by a three digit BCD number.

In the manual mode of operation, counter 53 is preset by gate length thumbwheel 57 through AND gates 71 and OR gates 72. In the automatic mode of operation gates 71 are not enabled while gates 74 are enabled by the mode signal in line 75 and counter 53 is preset from the computer. Counter 52 could, of course, be preset from the computer in the same manner if desired.

Figure 3:
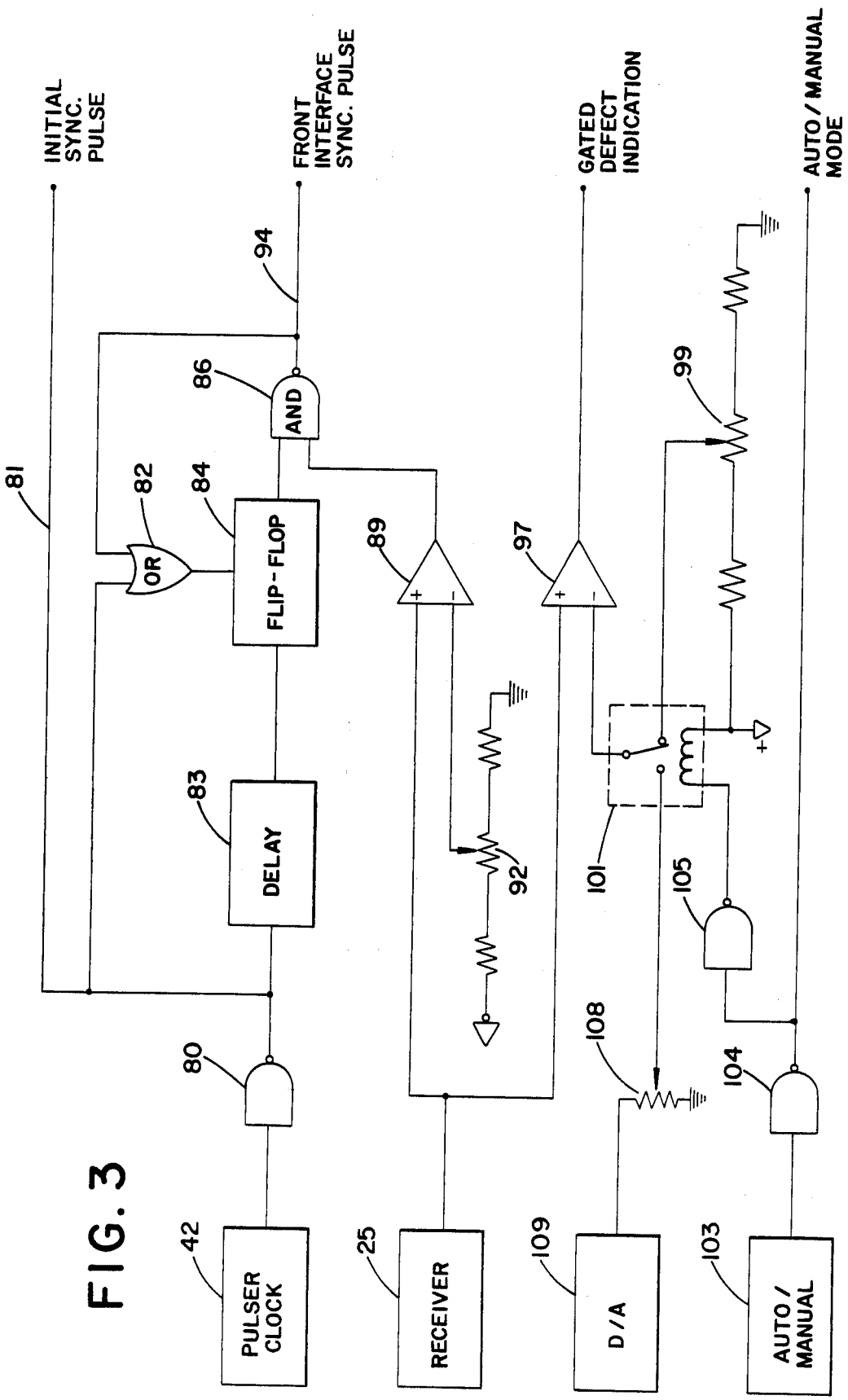
FIG. 3 is a block diagram of circuits for obtaining signals employed in the ultrasonic defect gate.

FIG. 3 illustrates the circuits for developing the control signals employed in the defect gate. The initial sync pulse is a trigger pulse from pulser clock 42 (FIG. 1) which is provided through an inverter 80 to line 81. A front interface sync pulse is generated by delaying the initial sync pulse in delay circuit 83 and then providing it to set flip-flop 84 which was previously cleared through OR gate 82. The output of flip-flop 84 enables an AND gate 86. The remaining input to gate 86 is from a comparator 89 which provides an output signal to gate 86 when a signal from receiver 25 (FIG. 1), exceeds a selected noise rejection level from a potentiometer 92. Thus, the front interface of the specimen 10 is detected as being the first reflection to receiver 25 having a magnitude above the noise rejection level. The front interface sync pulse is provided through gate 86 to OR gate 82 to clear flip-flop 84. The front interface sync pulse is also provided through line 94 to other circuits which employ it.

The output of receiver 25 is also connected to a comparator 97 which compares the magnitude of the reflected defect indications from the receiver with a threshold level and provides an output signal when the defect is greater than the threshold level. In the manual mode of operation the threshold level is manually set on a potentiometer 99 which has its output connected through a relay 101 to the input of comparator 97. In the automatic or computer controlled mode of operation relay 101 is actuated by a switch 103 through inverters 104 and 105. The input of comparator 97 is then connected to a potentiometer 108 which receives its input from a digital to analog converter 109 controlled by the computer. The output signal from comparator 97 is identified as a gated defect indication and is employed in the gate circuits as described below.

The circuit of FIG. 4 captures the magnitudes of the two largest gated defect indications occurring within a gate window. Each initial sync pulse triggers a one shot 120 which energizes the coil of a relay 122 through a driver 124. Actuation of relay 122 connects an initializing voltage from a source 126 through contacts 122a and 122b to the inputs of a pair of sample-hold units 129 and 130. It will be appreciated that relay 122 and its contacts may be replaced by an analog switch for faster operation. For easy reference, sample-hold unit 129 is associated with defect A while unit 130 is associated with defect B. One shot 120 also provides a sample command to each sample-hold unit 129, 130 through OR gates 134 and 135, respectively. Sample-hold unit 129 is thereby initialized to a slight positive voltage while sample hold unit 130 is initialized to zero volts. The output of sample-hold unit 129 is provided through a buffer 140 to one input of a voltage comparator 143 while the output of sample-hold unit 130 is provided through a buffer 145 to one input of another voltage comparator 146. The remaining input to each voltage comparator 143, 146 is connected to receiver 25.

The output of voltage comparator 143 is connected to one input of an AND gate 150 while the output of voltage comparator 146 is connected to one input of an AND gate 151. The outputs of sample-hold units 129 and 130 are also connected through their respective buffers 140, 145 to the two inputs of voltage comparator 153 which has its output connected directly to an input of AND gate 151 and through an inverter 155 to an input of AND gate 150. Another input to each of AND gates 150, 151 is a gated defect indication in line 160 from comparator 97 in FIG. 3. The remaining input to AND gates 150, 151 is from an AND gate 162 which has one input connected to a one shot 164 and the other through line 165 to the defect gate window signal from flip-flop 50 (FIG. 2). The output of AND gate 150 is connected to a one shot 168 while the output of AND gate 151 is connected to a second one shot 169. One shot 168 is connected to one input of an OR gate 172 and through OR gate 134 to the sample command input of sample-hold unit 129. Similarly, one shot 169 is connected to an OR gate 174 and through OR gate 135 to the sample command input of sample-hold unit 130.

Each one shot 168, 169 is also connected to the input of an OR gate 177 which provides a defect interrupt signal to the computer interface through line 178 and also initiates an audio alarm 179. Each one shot 168, 169 is also connected to a display unit 180 or 181 to indicate a defect. The output of OR gate 177 is also connected to the input of one shot 164 and through a time delay 182 and an OR gate 183 to the reset input of a peak detector 185. The remaining input to OR gate 183 is the defect gate window signal from flip-flop 50 (FIG. 2). The output of peak detector 185 is connected through normally closed contacts 122a and 122b of relay 122 to the data inputs of sample-hold units 129 and 130.

In operation, each initial sync pulse fires one shot 120 which energizes relay 122 and instructs sample-hold units 129 and 130 to store initializing signals from potentiometer 126. Sample-hold 129 is initialized to a small positive voltage while sample hold 130 is initialized to zero volts in order to avoid ambiguity at the output of voltage comparator 153. The initial sync also clears a bistable latch 190 and fires a one shot 191 which provides a timer enable signal through an OR gate 193 to the computer interface for purposes to be described below.

At the beginning of the defect gate window peak detector 185 is cleared and AND gates 150, 151 are enabled by AND gate 162. When a defect is detected above the threshold level a gated defect indication in line 160 from comparator 97 (FIG. 2) also enables AND gates 150 and 151. Meanwhile, the magnitude of the defect from receiver 25 is compared to the initialized values in sample-hold units 129 and 130 by comparators 143 and 146, respectively. Also, the initialized values in sample-hold units 129 and 130 are compared in comparator 153. Since the initialized value in sample-hold unit 129 is greater than that in sample hold unit 130 comparator 153 provides an enabling signal to AND gate 151 but not to AND gate 150. Comparator 146 determines that the defect magnitude is greater than the initialized value stored in sample hold unit 130 and provides the final enabling signal to AND gate 151 which causes it to fire one shot 169.

One shot 169 provides a sample command through OR gate 135 to sample-hold unit 130 to cause that unit to store the defect magnitude provided by peak detector 185 through relay contacts 122b. The output of one shot 169 is also provided to OR gate 174 which provides a defect B time strobe signal to the computer interface as described below. One shot 169 also fires inhibit one shot 164 through OR gate 177 to inhibit AND gates 150 and 151. Thus, for the period of one shot 164 no other defect indication can be provided. The period of one shot 164 is chosen to provide an appropriate inhibit duration so that two defect indications will not be given for a single defect or for two defects which are so closely spaced as to make it advantageous to consider them as only a single defect. The output of OR gate 177 also provides a defect interrupt signal to the computer interface as described below and triggers the audio alarm 179 to indicate a defect. The signal from OR gate 177 resets peak detector 185 after a time delay provided by delay unit 182.

If another defect is detected within the defect gate window but following the inhibit period provided by one shot 164, then the process described above is repeated. The new defect magnitude is compared to the magnitude of the stored value in both sample-hold unit 129 and 130 and is substituted in the unit storing the smaller value which would be unit A. Operation continues in the same manner during the defect gate window, so that at the end of the window sample-hold units 129 and 130 store the magnitudes of the two largest defects detected withhin the window. The magnitude of each defect stored is made available to the computer in lines 176 and 197. It will be apparent that additional circuitry may be provided, if desired, to store more than two defects detected within a gate window.

FIG. 5 illustrates the circuits for interfacing the defect gate with a digital computer. The interface communicates with the computer 41 (FIG. 1) through a digital bus indicated generally at 220. The computer may be a model PDP 11/40 manufactured by Digital Equipment Corporation of Maynard, Mass. Basically, the interface operates to accummulate data regarding the location and magnitude of the two defects stored within each gate window so that this information is available to the computer for analysis. The interface also relays output signals from the computer to the ultrasonic system for control thereof and data input thereto. Still further, the interface collects information from which the computer can determine the distance from the ultrasonic transducer to the front interface of the specimen under test.

The interface includes a 12-bit binary counter 225 which receives pulses from a clock 226 and has its output connected to three 12-bit registers 228, 229 and 230. Counter 225 is cleared by a timer enable signal from OR gate 193 (FIG. 4) and is enabled to count at the termination of the clear signal. Register 228 is connected through a sync circuit 235 to receive the front interface time strobe signal from AND gate 86 (FIG. 3). Similarly, register 229 is connected through a sync circuit 237 to receive the defect A time strobe signal from OR gate 172 in FIG. 4 and register 230 is connected through sync circuit 239 to receive the defect B time strobe signal from OR gate 174 in FIG. 4. Upon receipt of the respective strobe signals the count in counter 225 is loaded into the appropriate register 228, 229, 230. Each of the sync circuits 235, 237, 239 merely insures that loading of the respective registers is not initiated while the count is changing in counter 225.

Each of the registers 228, 229, 230 is also connected to receive a read signal in line 241 to read the contents of each register in turn into the computer. Register 228 is read first followed by register 229 after a delay provided by delay unit 243 and then register 230 after a delay provided by delay unit 245. The read signal to register 230 is also connected to one input of an OR gate 248 which provides a data reset signal to bistable latch 190 in FIG. 4. The other input to OR gate 248 is a system initialize signal from the computer.

A defect interrupt from OR gate 177 in FIG. 4 is provided to interrupt latches 252. Latches 252 are reset by a signal from the computer after interrupts have been honored. The defect A and defect B magnitude signals in lines 196 and 197, respectively, in FIG. 4 are provided to an analog to digital converter 260 in the interface so that the magnitude information is available in digital form to the computer.

Signals provided from the computer to the system and the defect gate are loaded into a register 263 and supplied through line drivers indicated at 265 and 266. A digital gate length signal comprising, for example, a three digit BCD code is supplied through line drivers 265 to line 58 in FIG. 2 to be loaded into counter 53 as described above. One signal provided through line drivers 266 is to relay 47 in FIG. 1 to direct the ultrasonic pulse to one or the other transducer and receiver channel. The other signals are to pulser clock 42 for selection and enabling of that clock to supply pulses to pulser 44 or to substitute external clock pulses for those from clock 42. The computer also provides a gate level signal through the digital to analog converter 109 to comparator 97 in FIG. 3.

In operation, if the system is operating under computer control or in the automatic mode, the gate length and gate level information will be provided by the computer to line 58 in FIG. 2 and comparator 97 in FIG. 3, respectively. Also the relay 47 in FIG. 1 will be controlled to select the desired transducer and receiver channel and either pulses from clock 42 in FIG. 1 or external clock pulses will be selected.

Upon receipt of an initial sync pulse as a timer enable signal from OR gate 193 in FIG. 4, counter 225 in the computer interface will be cleared and then enabled to count. When a front interface time strobe is received from AND gate 86 in FIG. 3 the contents of counter 225 will be loaded into register 228. Subsequently, a defect A time strobe and/or a defect B time strobe from one shots 168 or 169 in FIG. 4 will strobe the contents of counter 225 into registers 229 and 230, respectively. Also, a defect interrupt signal from line 178 in FIG. 4 will be coupled through OR gate 250 to set interrupt latch 252. If either the A defect or the B defect or both are replaced by defects of greater magnitude within the gate window a new defect A or defect B time strobe or both will clear their respective registers 229 and 230 and load the appropriate register or registers with the new count from counter 225.

Thus, at the end of the defect gate window register 228 will contain a count which is indicative of the time required for the ultrasonic pulse to travel from the transducer to the front interface of the specimen and therefore of the distance between the two. This information can help to reduce the number of specimen inspections required and/or can provide the data required to optimize subsequent machining operations to salvage specimens with defect indications. Register 229 contains information indicative of the location within the specimen of defect A and register 230 contains information indicative of the location of defect B. Also, the defect A and B magnitudes are present in digital form at the output of analog to digital converters 260.

The computer then has a period from the end of the gate window to the next initial sync pulse in which to collect the data available to it. This is done by providing a signal in line 241 to read the contents of registers 228, 229 and 230 and by reading the defect A and defect B magnitudes. After defect B register 230 is read a data reset signal is supplied through OR gate 248 to set bistable latch 190 in FIG. 4. The output from latch 190 is provided through OR gate 193 in FIG. 4 to clear and disenable counter 225. The output of bistable latch 190 also fires one shot 203 in FIG. 4 which provides a defect A time strobe to register 229 which loads the register with a zero count. One shot 203 in turn fires one shot 205 in FIG. 4 to produce a defect B time strobe to register 230 in the interface which loads that register with a zero count. On the next initial sync pulse, bistable latch 190 in FIG. 4 is cleared, counter 225 in the interface is enabled and operation proceeds again as described above.

To summarize the overall operation, each initial sync pulse occurs substantially simultaneously with a trigger pulse from pulser clock 42 in FIG. 1. Each initial sync pulse resets the down counters 52 and 53 to set the start and duration of the gate window in FIG. 2 and also clears and then enables counter 225 in the computer interface (FIG. 5). Each initial sync pulse also initializes sample-hold units 129 and 130 in FIG. 4 as described above. Upon receipt of the front interface sync pulse, register 228 in FIG. 5 is loaded with the contents of counter 225 and flip-flop 64 in FIG. 2 is set to enable pulses to be provided to down counter 52. When counter 52 reaches zero flip-flop 50 is set to begin the gate window and peak detector 185 in FIG. 4 is cleared. The defect gate window signal enables AND gate 150 and 151 in FIG. 4 through AND gate 162. Defect magnitudes are compared to the previous values stored in sample-hold units 129 and 130 as described above. Inhibit one shot 164 provides a minimum separation between defect indications as described above. When a defect is indicated an appropriate defect A or defect B time strobe is provided to register 229 or 230 in the computer interface in FIG. 5 and a defect interrupt is provided to latches 252. At the end of the gate window and before the next initial sync pulse, registers 228, 229 and 230 are read by the computer along with the defect A and defect B magnitudes and a data reset is provided through OR gate 248 to disenable counter 225 and clear the registers in the computer interface.

The computer can be programmed for real time diagnosis of the data provided to it and can, through the interface, modify the inspection parameters such as gate duration in real time to maximize the effectiveness of the inspection.

Figure 6:
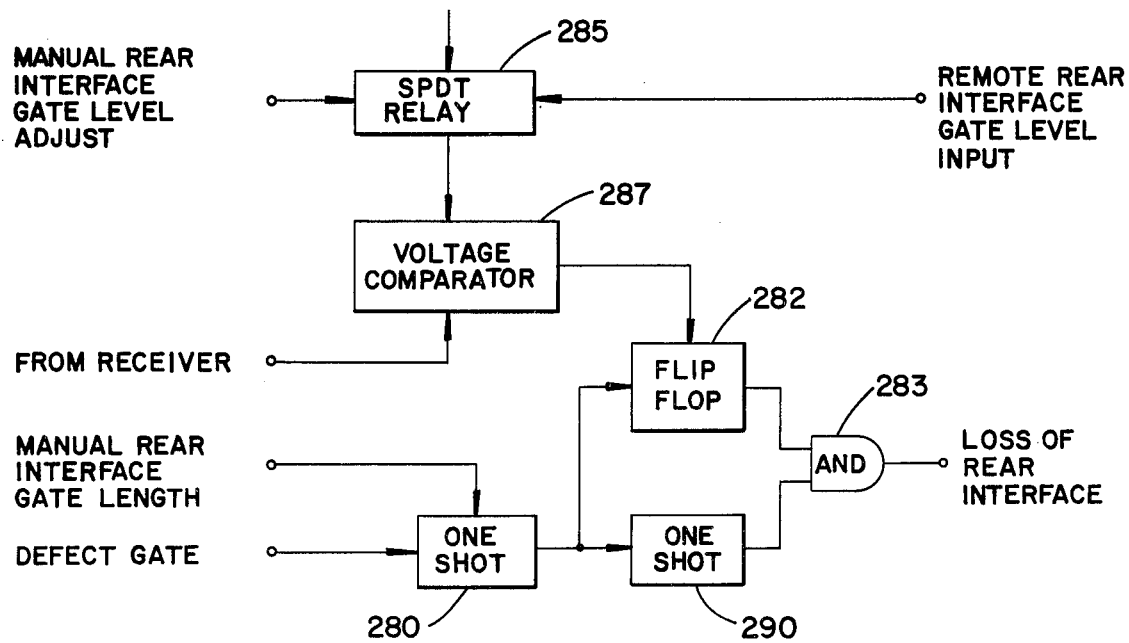
FIG. 6 is a block diagram of a circuit for detecting a specimen rear interface indication within a rear interface gate window.

FIG. 6 discloses a circuit for obtaining and providing additional information to the computer for assistance in analyzing the ultrasonic reflected signal characteristics. The circuit of FIG. 6 provides an additional gate window to determine when a reflection from the rear interface of the specimen is present or absent in the ultrasonic signal under examination. Such information can be quite useful in analyzing the ultrasonic signal characteristics.

As shown in FIG. 6, the rear interface gate window is established by a one shot 280 which is triggered on the trailing edge of a defect gate window signal from flip-flop 50 in FIG. 2. The leading edge of the signal from one shot 280 sets flip-flop 282 which has its output connected to an AND gate 283. A threshold level for the rear interface determination is provided either manually or from the computer through a single pole double throw relay 285 to one input of a voltage comparator 287. The remaining input to voltage comparator 287 is from the receiver, such as receiver 25 in FIG. 1. If the signal from the receiver exceeds the threshold level voltage comparator 287 provides a signal to reset flip-flop 282. A one shot 290 is triggered on the trailing edge of the signal from one shot 280 and is connected to an input of AND gate 283. If flip-flop 282 is reset during the rear interface gate window provided by one shot 280 and then AND gate 283 is not enabled to pass the pulse from one shot 290. If, however, flip-flop 282 is not reset then the signal from one shot 290 will pass through AND gate 283 to latches 252 in FIG. 5 as an interrupt to indicate absence of a rear interface indication in the ultrasonic signal.

While the rear interface gate period is illustrated as being provided by the one shot 280 it will be appreciated that the rear interface gate window can be established in the same manner as the defect gate window as shown in FIG. 2. In that case, a flip-flop corresponding to flip-flop 64 in FIG. 2 would be set on the trailing edge of the defect gate window signal provided by flip-flop 50 in FIG. 2.

What is claimed is:

1. Ultrasonic inspection apparatus comprising transducer means adapted to be coupled to a test specimen for transmitting an ultrasonic interrogating signal into said specimen and for receiving reflected signals therefrom indicative of defects in said specimen, means defining a defect gate window in which said defect signals are to be inspected, means for storing the magnitudes of a plurality of defect signals, means for comparing succeeding defect signals with the magnitudes of each of said stored defect signals, and means for causing the magnitude of a succeeding defect signal in said gate window which is greater than the magnitude of at least one of said stored defect signals to replace the smallest of said stored signals.

2. Apparatus as claimed in claim 1 further comprising means for inhibiting replacement of a defect signal for a predetermined time after a previous replacement.

3. Apparatus as claimed in claim 1 further comprising a source of clock pulses, a counter for counting said clock pulses, count storage means associated with each of said defect signal storage means for storing a count from said counter indicative of the location in said specimen of the stored defect, and means for updating a count storage means when a stored defect signal is replaced by a succeeding defect signal.

4. Apparatus as claimed in claim 1 wherein said defect gate window defining means includes a source of clock pulses, a first counter, a second counter, means for causing said first counter to provide a first output signal after counting a number of clock pulses indicative of the distance from a reference point to the beginning of said gate window, means for causing said second counter to provide a second output signal after counting a number of pulses indicative of the duration of said gate window, and bistable means assuming a first state in response to said first output signal for defining said gate window and assuming a second state in response to said second output signal for defining the end of said gate window.

5. Apparatus as claimed in claim 4 wherein said first counter is a preset down counter which is enabled to count coincident with a reflected signal from the front interface of said specimen, and wherein said second counter is a preset down counter enabled to count upon occurrence of said first output signal, and including means for presetting said counters.

6. Apparatus as claimed in claim 1 further comprising means defining a rear interface gate window following said defect gate window and in which a reflected signal from the rear interface of said specimen is expected to appear, and means for providing an output signal if a rear interface signal does not appear in said rear interface gate window.

7. Apparatus as claimed in claim 1 further comprising means for providing a signal indicative of the reflection of said interrogating signal from the front interface of said specimen, a source of clock pulses, a counter, count storage means, means coincident with said interrogating signal for enabling said counter to count said clock pulses, and means responsive to said front interface signal for transferring the count in said counter to said count storage means.

8. A method for ultrasonic inspection of a test specimen comprising the steps of transmitting an ultrasonic interrogating signal into said specimen, receiving reflected signals from said specimen indicative of defects therein, defining a defect gate window in which defect signals are to be inspected, storing a plurality of defect signals, comparing the magnitude of succeeding defect signals with the magnitude of each of said stored defect signals, and replacing the smallest of said stored signals with a succeeding defect signal in said gate window which is greater than at least one of said stored defect signals.

9. A method as claimed in claim 8 further comprising the step of inhibiting replacement of a stored signal for a predetermined time following a previous replacement.

10. A method as claimed in claim 8 further comprising the steps of defining a rear interface gate window following said defect gate window in which a reflected signal from the rear interface of said specimen is expected to appear, and providing an output signal if a rear interface signal does not appear in said rear interface gate window.

11. In ultrasonic testing in which an interrogating signal is transmitted to a test specimen and reflected signals are received indicative of defects in said specimen, controllable apparatus for use with control and diagnostic means for gathering data regarding said defects, said apparatus comprising means for defining a defect gate window corresponding to a depth range in which said specimen is to be inspected, means for determining the magnitudes and locations of the N largest defects in said gate window where N is an integer greater than 1, means for storing said magnitude and location data, and means for providing a signal indicating the availability of said data to said control and diagnostic means.

12. Apparatus as claimed in claim 11 wherein said defect gate window defining means includes a source of clock pulses, a first counter presettable by said control and diagnostic means for defining a starting point for said gate window, a second counter presettable by said control and diagnostic means for defining a duration for said gate window, means for enabling said first counter to count said clock pulses upon receipt of a reference signal, and means for enabling said second counter to count said clock pulses when said first counter has counted to said starting point.

13. Apparatus as claimed in claim 11 further comprising means for defining a rear interface gate window following said defect gate window and in which a reflected signal from the rear interface of said specimen is expected to appear, and means for providing a signal to said control and diagnostic means if a rear interface signal does not appear in said rear interface gate window.

14. In ultrasonic testing in which an interrogating signal is transmitted to a test specimen and reflected signals are received indicative of defects in said specimen, apparatus for use with control and diagnostic means for gathering data regarding said defects, said apparatus being controllable in real time by said control and diagnostic means to control test parameters in response to real time diagnosis of said data, said apparatus comprising means for defining a defect gate window corresponding to a depth range in which said specimen is to be inspected, means for enabling real time control of said defect gate window defining means by said control and diagnostic means, means for determining the magnitude and location of a defect in said gate window exceeding a predetermined level, means for enabling real time control of said predetermined level by said control and diagnostic means, means for storing said magnitude and location data, means for providing a signal indicating the availability of said data to said control and diagnostic means, means for defining a rear interface gate window following said defect gate window, means for detecting a reflected signal exceeding a predetermined level in said rear interface gate window indicative of the rear interface of said specimen, amd means for enabling real time control of the duration of said rear interface gate window and of said predetermined value by said control and diagnostic means.

* * * * *